United States Patent [19]

Tschunt

[11] 4,219,733
[45] Aug. 26, 1980

[54] X-RAY DIAGNOSTIC APPARATUS PRODUCING TRANSVERSE LAYER IMAGES

[75] Inventor: Edgar Tschunt, Rathsberg, Fed. Rep. of Germany

[73] Assignee: Siemens Aktiengesellschaft, Berlin & Munich, Fed. Rep. of Germany

[21] Appl. No.: 875,385

[22] Filed: Feb. 6, 1978

[30] Foreign Application Priority Data

Apr. 1, 1977 [DE] Fed. Rep. of Germany ....... 2714759

[51] Int. Cl.² .......................................... G03B 41/16
[52] U.S. Cl. .............................. 250/445 T; 250/360
[58] Field of Search ........................... 250/445 T, 360

[56] References Cited

U.S. PATENT DOCUMENTS

| | | | |
|---|---|---|---|
| 3,922,552 | 11/1975 | Ledley | 250/445 T |
| 4,031,395 | 6/1977 | Le May | 250/445 T |
| 4,137,455 | 1/1979 | Fetter | 250/445 T |

*Primary Examiner*—Craig E. Church
*Attorney, Agent, or Firm*—Hill, Van Santen, Steadman, Chiara & Simpson

[57] ABSTRACT

In an illustrated embodiment, the fan-shaped x-ray beam is rotated by electronic switching and a detector ring is gimbaled so that only the desired sector thereof intercepts the beam. A collimator ring may be rotated in step with the beam and have a pin and slot coupling with the detector ring to control the swiveling thereof.

3 Claims, 4 Drawing Figures

X-RAY DIAGNOSTIC APPARATUS PRODUCING TRANSVERSE LAYER IMAGES

BACKGROUND OF THE INVENTION

The invention relates to an x-ray diagnostic apparatus for producing transverse layer images of a radiography subject with an x-ray measuring arrangement comprising an x-ray source which produces a fan-shaped beam of x-rays penetrating the radiography subject, the cross-sectional extent of the beam perpendicular to the layer plane being equal to the layer thickness and in the layer plane being of a magnitude such that the whole layer is penetrated with radiation, and comprising also a radiation receiver which ascertains the transmitted radiation intensity, said radiation receiver being constructed as a circular ring into which the radiography subject may be inserted and consisting of a series of detectors, and with means for changing the direction of the x-ray beam's axis of symmetry, and with a computer for the transformation of the signals supplied by the radiation receiver into a layer image.

Described in U.S. Pat. No. 3,778,614 is an x-ray diagnostic apparatus which has all these features apart from the circular radiation receiver. In this known x-ray diagnostic apparatus, the radiation receiver is laterally displaceable. When the subject is scanned, lateral displacement movements and rotational movements through a prescribed angle, e.g. 1°, follow one another alternately until the entire subject is scanned. From the measured absorption values the computer calculates the transverse layer image in the form of a matrix of image point data. The drawback with this x-ray diagnostic apparatus is that, because of the necessary mechanical movement of the radiation receiver and the x-ray tube, the time required for an image exposure is relatively long.

In the publication "Computerized Tomographic Scanner" issued by American Science and Engineering, Inc., publication number ASE-3869, an x-ray diagnostic apparatus of the type stated at the beginning is described. This x-ray diagnostic apparatus thus has a circular radiation receiver which encloses the radiography subject. All that is necessary is a rotational movement of the x-ray source disposed inside the radiation receiver, but no movement of the radiation receiver. The time required for an image exposure is therefore reduced relative to the apparatus known through U.S. Pat. No. 3,778,614. Furthermore, a simpler mechanical structure also results.

SUMMARY OF THE INVENTION

The object underlying the invention is to improve still further an x-ray diagnostic apparatus of the type specified at the beginning with respect to the image exposure time required. The purpose of the invention, in particular, is to create an apparatus of a type in which the mechanical movements are reduced to a minimum.

According to the invention, this object is achieved by virtue of the fact that the x-ray source comprises a hollow evacuated glass ring arrangement, concentrically encircling the radiation receiver, in which hollow ring arrangement a circular anode arrangement is disposed and opposite said anode arrangement a number of cathodes are disposed, the number being dependent on the desired measured value number, that there are means present for the step-by-step actuation of the electron radiation between at least one cathode, respectively, and the anode arrangement, that the radiation receiver is mounted on gimbals and that it is acted upon by guide means which are so designed that they swivel into the x-ray beam the particular part of the radiation-receiver which is required for detecting the x-radiation issuing from the radiography subject. In the case of the x-ray diagnostic apparatus according to the invention, a rotational movement of the x-ray beam is effected in a purely electronic manner by step-by-step successive releasing of the electron radiation between one cathode, respectively, and the anode. Since the x-ray source encircles the radiation receiver coaxially, the gimbal mounting of the radiation receiver and its turning movement ensures that the incident x-ray beam bypasses laterally past the radiation receiver and only impinges on it after it has penetrated the radiography subject. A minimum of mechanical movements is sufficient for the apparatus according to the invention to effect a scan of the radiography subject. The exposure time can therefore be very short.

Within the scope of the invention, a collimator can be mounted within the radiation receiver capable of rotation about the axis of the x-ray source and the radiation receiver, the lamellae of which are aligned with the rays from the x-ray source and which is connected to the radiation receiver by pins guided in a groove. In this way, the pivoting movement of the radiation receiver takes place automatically as the collimator rotates.

The invention is explained in more detail below with reference to an embodiment represented in the accompanying sheets of drawings; other objects, features and advantages will be apparent from this detailed disclosure and from the appended claims.

DETAILED DESCRIPTION

Figure 1:
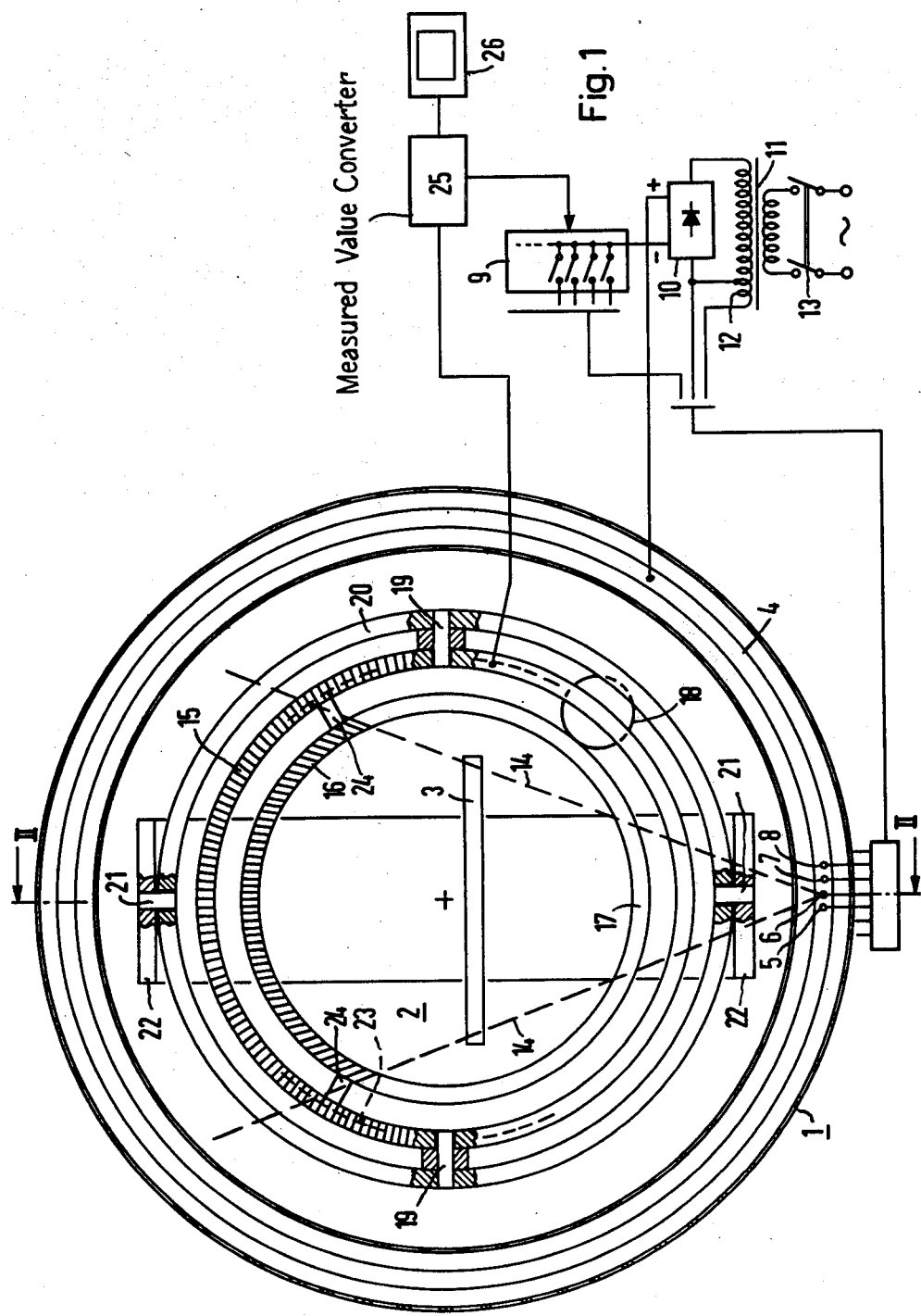
FIG. 1 is a diagrammatic vertical sectional view of an x-ray diagnostic apparatus according to the invention.
Figure 2:
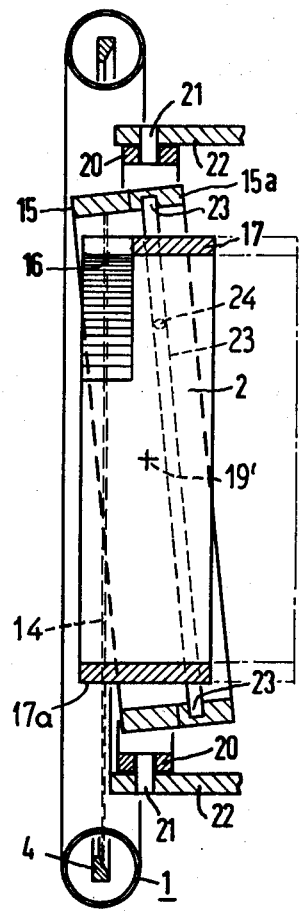
FIG. 2 shows a diagrammatic longitudinal sectional view taken generally as indicated by the line II—II in FIG. 1.
Figure 3:
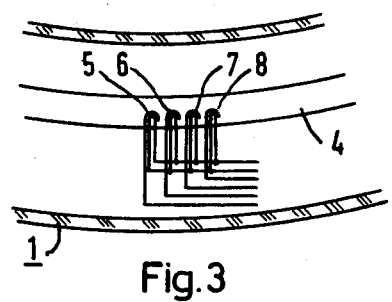
FIGS. 3 and 4 show details of the apparatus according to FIGS. 1 and 2.

The apparatus according to FIGS. 1 and 2 has an x-ray source 1, designed as an evacuated hollow glass ring or tube, which encircles a concentric opening 2. In the opening 2, a patient is supported on a couch 3 which is not represented in FIG. 2 for the sake of clarity. According to FIG. 3 the x-ray tube 1 contains a circular anode 4 with which a plurality of cathodes 5 to 8 etc. are associated. The cathodes 5 to 8 etc. are all preheated via appropriate heating coils during an exposure and shortly before an exposure. The production of the x-radiation, issuing from the anode 4, at a particular point proceeds by connecting one of the cathodes 5 to 8 etc., respectively, via a switching device 9, to the negative pole of a high voltage rectifier 10. The positive pole of the high voltage rectifier 10 is connected to the anode 4. The high voltage rectifier 10 is supplied by a high voltage transformer 11 which, on its secondary side, has a heating winding 12 which effects the heating of the heating coils of the cathodes 5 to 8 etc. The primary winding of the high voltage transformer 11 is connectable to the power supply via a main switch 13.

Figure 4:
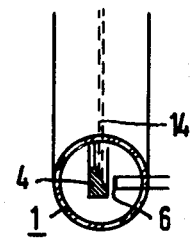

The shape of the anode 4 in cross-section is revealed clearly from FIG. 4. The x-radiation issues from it as a fan-shaped beam 14, the direction of which is dependent on the particular cathode 5 to 8 etc., which is actuated by means of the switching device 9. The structural parts, particularly the x-ray tube 1, are not drawn to scale in the figures.

In the sample embodiment, the x-ray beam 14 is emitted straight (radially inwardly) from the anode 4. To examine a patient lying on the couch 3, the cathodes 5 to 8 etc. and further cathodes extending along the entire anode 4, are actuated progressively (in step-by-step fashion), so that the direction of the x-ray beam 14 changes progressively. The x-ray beam is thus rotated progressively in a clockwise or a counter-clockwise direction. In practice, an expedient method is to provide 360 cathodes, for example, and to rotate the x-ray beam 14 by one degree each time, so that, after a complete rotational movement has been completed, the beam has been rotated through 360 degrees.

The x-ray beam 14 issuing from the patient lying on the couch 3 is detected by a circular radiation receiver 15 consisting of a series of individual detectors. The number of individual detectors is selected according to the desired image resolution. Impingement is always on a number of individual detectors corresponding to the angle of aperture of the fan-shaped x-ray beam. The detectors which are impinged upon in each instance depends on the particular cathode activated at the time. The radiation receiver 15 is not rotated while the patient is being scanned; during scanning the x-ray beam 14 is rotated round the patient by means of sequence switch 9.

Situated in front of the x-ray receiver 15, viewed in radiation direction, is a collimator 16 whose lamellae are aligned with the active focus of the anode 4 of the x-ray source 1. The collimator 16 is attached to a ring 17 which is rotated by a drive device 18, while a patient is being scanned, such that the lamellae of the collimator 16 are always aligned with the particular active focus of the x-ray tube 1.

In the case of the x-ray apparatus according to FIGS. 1 to 4, it is ensured that the x-ray beam 14 first runs laterally past the radiation receiver 15, then penetrates a radiation-permeable part 17a of the ring 17 and subsequently the patient and the collimator 16. Thereafter, the x-ray beam 14 impinges on the radiation receiver 15. This is clear from FIG. 2. FIGS. 1 and 2 show that in order to achieve this objective, the radiation receiver 15 is mounted on a carrier ring 20 by means of two bearings 19, FIG. 1, with the ability to swivel about a horizontal axis (indicated at 19', FIG. 2), and that the carrier ring 20 is mounted in two bearing brackets 22 carrying two bearings 21 which provide for swiveling of the carrier ring 20 about a vertical axis. The radiation receiver 15 is thus mounted on gimbals and is universally pivotable. A ring 15a bearing the receiver 15 has a circular groove 23 on its inside which is particularly visible in FIG. 2. In the groove 23, two pins 24 (FIG. 1) are guided by means of roller bearings disposed at the ends of pins 24 and engaging one of the side walls of the groove 23, the pins 24 being fixed to the collimator ring 17. The pins 24 have the effect that only that part of the radiation receiver 15, which is required for detecting the x-radiation issuing from the radiography subject is swivelled into the x-ray beam 14. All other parts of the radiation receiver 15 lie outside the x-ray beam 14.

When the x-ray beam 14 is rotated, the collimator ring 17 with the collimator 16 is correspondingly rotated at the same time and thus causes the radiation receiver 15 to swivel in the manner illustrated via the pins 24 guided in the groove 23. The mechanical movements are restricted to a minimum in the x-ray apparatus described. There is merely a slight swivelling movement of the radiation receiver 15 and simple circular rotation of the relatively light collimator ring 17.

It is also clear from FIG. 1 that the radiation receiver 15 is connected to a measured value converter or computer 25 which calculates from the output signals of the individual detectors of the radiation receiver 15 the attenuation values of predetermined points of the irradiated layer of the patient in the form of a matrix and effects the reproduction of the image of this layer on a video device 26. The computer 25 controls the switching device 9 for the step-by-step actuation of cathodes 5 to 8 etc. It is also clear from FIGS. 1 and 2 that the x-ray beam 14 penetrates the patient completely in the transverse layer to be examined and that, perpendicularly to this layer, it has an extent which is equal to the thickness of this layer.

Within the scope of the invention the x-ray source need not have a single glass ring or toroidal envelope accommmodating the anode and the cathodes. It is also possible to construct the x-ray source from tubular ring segments.

As shown in FIG. 1, for each position of the x-ray beam 14, the collimator 16 has a corresponding position with the laminellae thereof aligned with respective rays of the x-ray beam from the active focus. The arcuate extent of the beam 14, FIG. 1, corresponds to the active extent of the collimator 16, the guide pins 24 being located at the margins of the beam 14 and having an angular separation generally corresponding to the arcuate width of beam 14 where it impinges on the radiation receiver 15.

Reference is made to my copending application Ser. No. 817,209 filed July 20, 1977, and the disclosure of said copending application is incorporated herein by reference.

In the embodiment illustrated in the present drawings, the plane of the fan-shaped beam 14 corresponds to the radial plane of the focii of anode 4 as indicated in FIG. 4, the axis of symmetry of the beam 14 being directed radially of anode 4.

It will be apparent that many modifications and variations may be effected without departing from the scope of the novel concepts and teachings of the present invention.

I claim as my invention:

1. An x-ray diagnostic apparatus for producing transverse layer images of a radiography subject with an x-ray measuring arrangement comprising an x-ray source which produces a fan-shaped x-ray beam penetrating the ratiography subject, the cross-sectional extent of the beam, perpendicular to the layer plane, being equal to the layer thickness and, in the layer plane, being of such a magnitude that the entire layer is penetrated with radiation, and comprising also a radiation receiver which detects the radiation intensity emanating from the layer, said radiation receiver being constructed as a circular ring into which the radiography subject may be inserted and comprising a series of detectors, and with means for changing the direction of the axis of symmetry of the x-ray beam to effect a scanning operation and with a measured value converter for the transformation of the signals supplied by the radiation receiver into a layer image, characterized in that the x-ray source (1) comprises an evacuated tube means disposed outwardly of the radiation receiver (15), anode means (4) in the tube means, and a number of cathodes (5 etc.) opposite successive portions of the anode means (4) for producing a desired number of measured values, in that there are means (9) present for the progressive actuation of electron radiation between at least one of said cathodes (5 etc.), respectively, and the anode means (4) to effect a scanning operation, in that the radiation receiver (15) has gimbal mounting means, and guide means (24) acting on said radiation receiver (15) for swiveling that particular part of the circular ring forming the radiation receiver (15), which is required to detect the x-radiation issuing from the radiography subject, into the x-ray beam (14), such that successive parts of the circular ring forming the radiation receiver are successively interposed between the radiography subject and portions of the x-ray source outwardly thereof during a scanning operation.

2. Apparatus according to claim 1, characterized in that, inside the radiation receiver (15), a collimator (16) is rotatably mounted about the axis of the x-ray source (1) and the radiation receiver (15), the collimator (16) having lamellae which are aligned with ray paths from the x-ray source (1), and the collimator (16) and the radiation receiver (15) having said guide means acting therebetween in the form of a pin (24) and groove (23) coupling.

3. Apparatus according to claim 2, characterized in that a ring (15a) carries the radiation receiver (15), coaxially therewith, the coupling comprising pins (24) disposed in arcuately spaced relation on the collimator (16) and having an arcuate separation corresponding to the arcuate width of the x-ray beam (14, FIG. 1) impinging on the radiation receiver (15).

* * * * *